(12) United States Patent
Cull et al.

(10) Patent No.: US 8,162,919 B2
(45) Date of Patent: Apr. 24, 2012

(54) FLOW CONTROL SYSTEM BASED ON LEAKAGE

(75) Inventors: Laurence J. Cull, Woods Cross, UT (US); James T. Perkins, St. Charles, MO (US); Russ Finlay, San Clemente, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 120 days.

(21) Appl. No.: 12/329,863

(22) Filed: Dec. 8, 2008

(65) Prior Publication Data

US 2010/0145302 A1 Jun. 10, 2010

(51) Int. Cl.
*A61M 37/00* (2006.01)

(52) U.S. Cl. .......................................... 604/505; 604/66

(58) Field of Classification Search .................. 604/505, 604/66, 67, 30, 151; 128/230
See application file for complete search history.

(56) References Cited

U.S. PATENT DOCUMENTS

| | | | |
|---|---|---|---|
| 3,693,613 A | 9/1972 | Kelman | |
| 3,812,855 A | 5/1974 | Banko | 128/276 |
| 3,920,014 A | 11/1975 | Banko | 128/230 |
| 4,007,742 A | 2/1977 | Banko | 128/230 |
| 4,019,514 A | 4/1977 | Banko | 128/230 |
| 4,041,947 A | 8/1977 | Weiss | |
| 4,117,843 A | 10/1978 | Banko | 128/230 |
| 4,841,984 A | 6/1989 | Armeniades et al. | 128/748 |
| 5,733,256 A | 3/1998 | Costin | |
| 5,865,764 A | 2/1999 | Moorhead | 600/561 |
| 7,326,183 B2 | 2/2008 | Nazarifar et al. | 604/30 |
| 2003/0028141 A1* | 2/2003 | Kadziauskas et al. | 604/67 |
| 2007/0000301 A1 | 1/2007 | Todd et al. | 73/1.25 |
| 2007/0073234 A1 | 3/2007 | Nazarifar et al. | 604/151 |
| 2007/0083150 A1 | 4/2007 | Nazarifar et al. | 604/31 |

FOREIGN PATENT DOCUMENTS

WO WO 2007/001929 A2 1/2007

OTHER PUBLICATIONS

International Search Report (PCTISA/210) and Written Opinion (PCT/ISA/237) mailed on Jul. 22, 2010.

* cited by examiner

*Primary Examiner* — Jackie Ho
*Assistant Examiner* — Brandy C Scott
(74) *Attorney, Agent, or Firm* — Jeffrey B. Powers

(57) ABSTRACT

An ophthalmic surgical system utilizes a needle through which fluid is aspirated from a surgical site, and a sleeve coaxially received over the needle to define a flow passage between the sleeve and needle through which fluid is communicated to the surgical site. The system further includes a container that provides an adjustable infusion pressure for urging the flow of irrigation fluid to the surgical site. An aspiration pump urges aspiration of fluid from the surgical site, and a sensor detects the rate of aspiration flow. A controller is configured to calculate an intraocular eye pressure based on the infusion pressure and a pressure drop due to a resistance to the flow rate, which flow includes the sensed flow rate and a predicted leakage selected from a look-up table based on a size of the needle, a size of a sleeve, and a size of an incision through which the needle and the sleeve are placed.

5 Claims, 4 Drawing Sheets

FLOW CONTROL SYSTEM BASED ON LEAKAGE

FIELD

The present invention is related to ophthalmic microsurgical systems and more specifically, to ophthalmic microsurgical systems controlling the flow of fluids into and out of an eye being operated on.

BACKGROUND

The statements in this section merely provide background information related to the present disclosure and may not constitute prior art.

Ophthalmic surgical procedures on the eye generally require cutting and/or making an incision through which a phacoemulsification (phaco) or other type of instrument is inserted into the interior portion of the eye. The use of microsurgical needles or cannulas in ophthalmic surgery is well known, and phaco needles are typically inserted via an incision of about 4 millimeters or less. The surgeon may cause a flow of fluids for aspiration from the site during the eye surgery. However, it is important to prevent collapsing the eye or over-pressurizing the eye to avoid trauma on the retina, i.e., the separation of the retina from the choroid, a retinal tear, or, other damage to the eye. The introduction of fluids and application of suction for aspirating fluids from the eye may accordingly pose certain risks.

SUMMARY

In accordance with one aspect of the present application, an ophthalmic surgical system is provided that includes a sleeve coaxially received over a needle so as to define a flow passage between the sleeve and the needle through which irrigation fluid is communicated to a surgical site. The needle includes a central passage through which fluid is aspirated from the surgical site, where the sleeve and needle are inserted into an eye, through an incision of a predetermined size. The system further includes a container that is configured to be adjustably elevated above the surgical site, and provides an adjustable infusion pressure for urging the flow of irrigation fluid within the container towards the sleeve for infusion to the surgical site. The system includes a vacuum source that is configured to establish a vacuum pressure, for urging the aspiration of fluid from a surgical site through the passage in the needle. The system further includes a sensor for providing a signal indicative of the vacuum being applied, and a flow sensing or estimating device for providing a signal indicative of the rate that fluid is being aspirated from the surgical site. The system includes a controller that is configured to receive the input of a needle size, a sleeve size, and an incision size. The controller is configured to estimate an intraocular eye pressure based on the infusion pressure, less a pressure drop due to a predetermined resistance to the irrigation flow, as determined by the combination of the sensed fluid flow rate and a predicted leakage rate of fluid exiting the incision. The predicted leakage rate exiting the incision is select from a look-up table, based on values of the needle size, sleeve size, incision size, and the infusion pressure. The controller uses the predicted leakage rate for estimating the total irrigation flow, to obtain a more accurate estimate of intraocular eye pressure. This estimated intraocular eye pressure may be used in controlling the infusion pressure, to thereby adjust irrigation flow to maintain a desired intraocular eye pressure.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Various embodiments and their advantages are best understood by referring to FIGS. 1 through 4 of the drawings, like numerals being used for like and corresponding parts of the various drawings.

Figure 1:
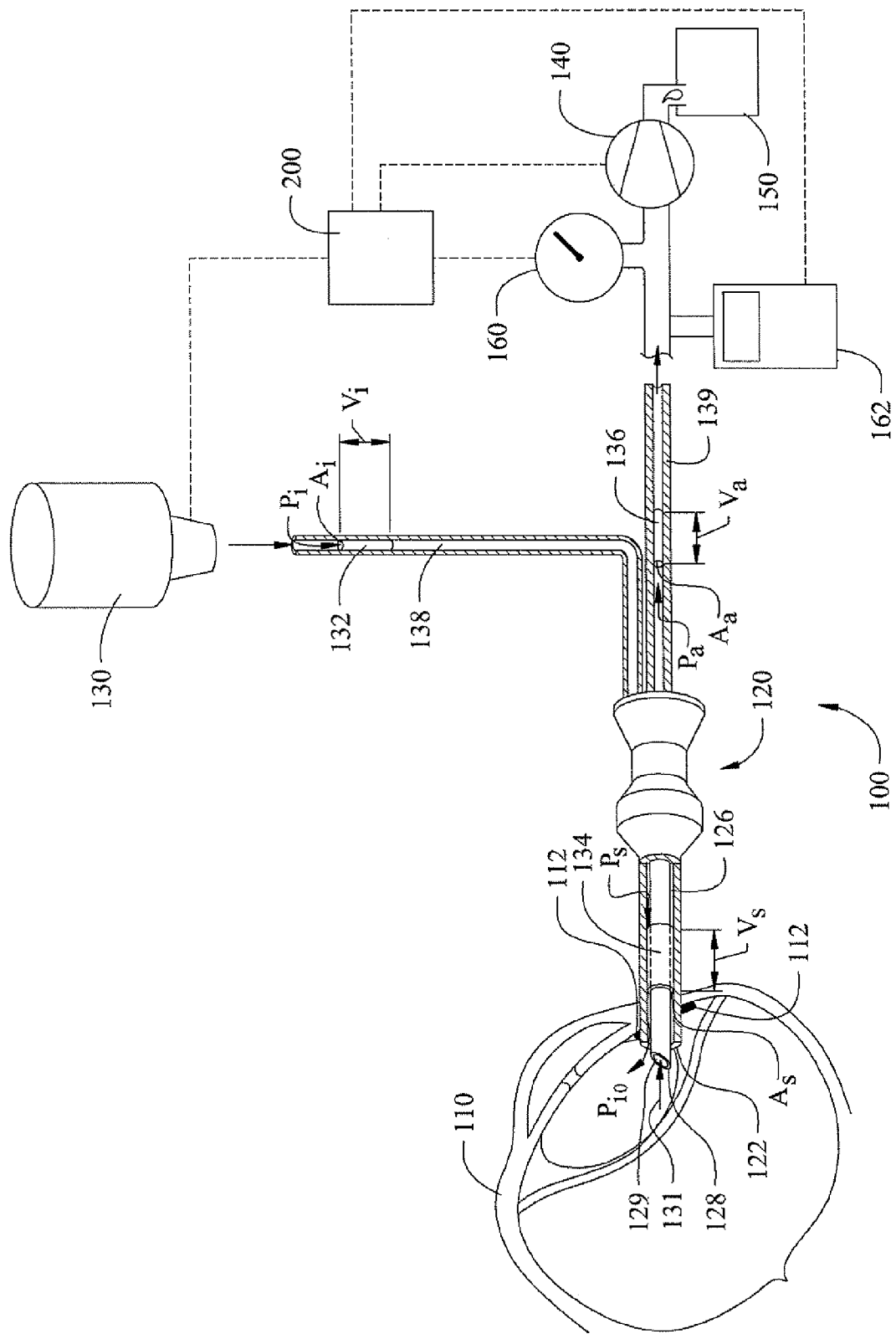
FIG. 1 shows a cross-sectional perspective view of one embodiment of a needle and aspiration flow control system in accordance with the present invention.

FIG. 1 shows one embodiment of an ophthalmic surgical system 100, in which fluid flow into and out of an eye 110, through an incision 112, is regulated or controlled to thereby control the intraocular eye pressure in the eye 110. The system 100 comprises an ophthalmic device 120 having a sleeve 122 coaxially received over a needle 128, such as in a phaco needle. The ophthalmic device 120, shown in FIG. 1, includes a sleeve 122 coaxially received over a needle 128, so as to define a flow passage 126 between the sleeve 122 and the needle 128, through which irrigation fluid is communicated to a surgical site (eye 110). The needle includes a central needle passage 129, through which fluid is aspirated from the surgical site, where the sleeve 122 and needle 128 are inserted into a medium such as an eye, through an incision 112 of a predetermined size.

The system 100 further includes a container 130 that is configured to be adjustably elevated above the surgical site, and provides an adjustable infusion pressure for urging the flow of irrigation fluid within the container 130 towards the sleeve 122 for infusion to the surgical site. The system includes a vacuum source 140 that is configured to establish a vacuum pressure, for urging the aspiration of fluid from a surgical site through the passage in the needle 128.

The system further includes a sensor 160 for providing a signal indicative of the vacuum being applied, and a flow sensing device 162 for providing a signal indicative of the rate that fluid is being aspirated from the surgical site. The system includes a controller 200 that is configured to receive the input of at least a needle size, a sleeve size, and an incision size. These inputs may be provided by a surgeon, for example. The controller 200 is configured to estimate an intraocular eye pressure based on the infusion pressure, less a pressure drop due to a predetermined resistance to the irrigation flow. It should be noted that the infusion pressure at the container 130 may be determined simply by the height of the container 130 above the eye 110, or by a device for measuring a value indicative of the infusion pressure (such as the container height), or by a pressure sensor. The irrigation flow entering the eye is determined by the combination of the sensed fluid flow rate (determined by sensor 160) and a predicted leakage rate of fluid exiting the incision 112. The predicted leakage rate exiting the incision 112 may be selected from a look-up table, based on values of the needle size, sleeve size, incision size, and the infusion pressure. Since the total fluid flow entering the eye is equal to the aspiration flow out of the eye and the leakage flow, the controller uses the predicted leakage rate for estimating the total irrigation flow, to obtain a more accurate estimate of intraocular eye pressure. This estimated intraocular eye pressure may be used in controlling the infusion pressure, to thereby adjust irrigation flow to maintain a desired intraocular eye pressure. Obviously, assuming unobstructed flow, the irrigation flow rate will typically be set higher than a desired flow rate that did not account for leakage.

The relationship between irrigation flow and infusion pressure may be understood in view of the following explanation. Under the Bernoulli principle, the total pressure is constant along a streamline for a particular fluid system. The total fluid pressure may be given by Bernoulli's equation:

$$\rho v^2/2 + \rho g h + p = C$$

where $\rho v^2/2$ is the dynamic pressure, $\rho g h$ is the head pressure associated with fluid free-falling from a height h above a reference, and $\rho$ is the static pressure, or pressure at a given point in a steady flowing fluid. As shown in FIG. 1, the flow velocity v may be affected by different cross-sectional areas ($A_i$ and $A_s$) in two sections along the streamline. For example, the fluid portion 132 may represent the flow rate $v_i$ of irrigation fluid flowing out of the irrigation bottle 130, and the fluid portion 134 may represent the flow rate $v_s$ of irrigation fluid flowing between the coaxially arranged sleeve 122 and needle 128. Similarly, the fluid portion 136 may represent the flow rate $v_a$ of fluid through the aspiration line 139. Assuming conservation of fluid flow, the various flow velocities may be related by the following equation, for example:

$$\rho v_i A_i v_i^2/2 + \rho v_i A_i g h_i = \rho v_s A_s v_s^2/2 + \rho v_s A_s g h_s$$

where $\rho v_i A_i v_i^2/2$ is associated with kinetic energy and $\rho v_i A_i g h_i$ is associated with potential energy.

From the above, it can be deduced that a difference in height between $h_i$ and $h_s$ will cause the irrigation fluid at rest in bottle 130 to establish a flow velocity that increases as the fluid falls through the irrigation line 138 towards the sleeve 122. Likewise, a reduction in cross-sectional area between two points in the infusion line at can also affect the fluid flow velocity between the two points. From the above, it should be understood that the flow rate or pressures in the two or more sections along a streamline can be determined using the basic equations above.

In applying the above equations to the system of FIG. 1, the absolute pressure in the eye 110 can be determined from the atmospheric pressure $p_o$, the head pressure of the irrigation fluid due to the bottle height, less the pressure drop through the irrigation line 138. It should be noted that the flow in the irrigation line 138 may be affected by flow restrictions $\Omega_i$ in the irrigation line, which act against the head pressure to impede the infusion flow rate Q (or $\rho v_i A_i$).

The pressure of the fluid exiting the irrigation line 138 may be determined from the pressure $p_{ib}$ of the irrigation bottle less the change in pressure $\Delta p_i$ along the irrigation line, and may be expressed as:

$$P_i = p_{ib} - \Delta p_i$$

Similarly, the pressure of the fluid being aspirated may be determined from the pressure $p_o$ at the collection reservoir 150 (the pressure measured by sensor 160 associated with a vacuum pump device 140, for example), less the change in pressure $\Delta p_a$ along the aspiration line, and may be expressed as:

$$P = \Delta p_a + p_o$$

Assuming no leakage of fluid out of the eye through the incision, the intraocular pressure in the eye ($p_{eye}$) for the system in FIG. 1 can be represented by the equation:

$$p_{ib} - \Delta p_i = p_{eye} = \Delta p_a + p_o$$

where $p_{ib}$ is the pressure of the fluid in the irrigation bottle 130, and $\Delta p_i$ is equal to:

$$\Delta p_i = (Q \cdot \Omega_i)$$

and $p_o$ is the pressure or vacuum at the collection reservoir 150, and $\Delta p_a$ is related to the resistance $\Omega_a$ in the aspiration line, as given by:

$$\Delta p_a = (Q \cdot \Omega_a)$$

By knowing the bottle height (or the infusion pressure at the bottle 130), the needle cannula 128 inner and outer diameters, the sleeve 122 inner diameter and sleeve area 126, we can predict an intraocular pressure based on the flow rate and vacuum. Specifically, the resistance to irrigation flow $\Omega_i$ and resistance to aspiration flow $\Omega_a$ can be predetermined, using lab data to develop an estimate of a predetermined flow resistance associated with the irrigation and aspiration flow lines typically employed in ophthalmic surgical procedures. The aspiration flow rate Q, infusion pressure at the bottle $p_{ib}$ and aspiration/vacuum pressure $p_v$ can be measured. It is accordingly possible to monitor the flow rate Q of fluid aspirated from the eye, and to control the infusion pressure at the bottle $p_{ib}$ and/or vacuum pressure $p_v$, to maintain a constant intraocular pressure by adjusting the infusion pressure $p_{ib}$ of the irrigation fluid in the bottle 130 (by adjusting the bottle height or by adjusting the bottle pressure). From the above data, intraocular pressure can be estimated and used as a surgical parameter.

The prediction of intraocular pressure can be accomplished by the method shown in the flow chart in FIG. 2, for example, which calculates the absolute pressure in the eye $P_{eye}$ based on the irrigation flow as follows:

$$P_{eye} = P_o + P_{ib} - (Q \cdot \Omega_i) \qquad \text{equation (1)}$$

where $P_o$ is the Atmospheric pressure, $P_{ib}$ is the head pressure due the height of the infusion bottle 130, Q is the irrigation flow rate (equal to the aspiration flow rate, assuming no leakage) and $\Omega_i$ is the resistance to irrigation flow through the tubing.

At step 310, the surgeon or user enters into the controller 200 a configuration for the device, which may be detected by a bar code or other similar method, from which the size of the needle and sleeve may be entered. The incision size may is also entered by the surgeon. It should be noted that the predetermined resistance to irrigation flow $\Omega_i$ may be stored as a default within the controller 200 as part of a look-up table, for example, or the flow resistance associated with the geometry of the particular device may be entered via bar code or by the user. The pressure $P_{ib}$ of the irrigation fluid in the irrigation bottle 130 is then set, by adjusting the bottle height, or pressurization of the infusion bottle, etc. The system then monitors fluid flow rate using a positive displacement pump, a flow sensor, electromagnetic flow technology, or other similar flow sensing or estimating technology. From the resistance to irrigation flow $\Omega_i$ identified in a look-up table and the infusion pressure at the bottle $P_{ib}$, the intraocular pressure $P_{eye}$ of the eye is determined as outlined in equation 1 above, for example. The intraocular pressure $P_{eye}$ may be displayed on a Graphical User Interface (not shown). Once the Intraocular pressure $P_{eye}$ is determined, the infusion pressure $P_{ib}$, vacuum $P_v$, or flow Q can be adjusted to maintain a constant desired intraocular pressure $P_{eye}$.

However, the above determination assumes no leakage of fluid out of the eye through the incision. Where there is a difference between the size of the incision 112 and the size of the needle 128 and/or sleeve 122 of a phaco-needle, some leakage of fluids may occur. As an example, the incision tool used by the surgeon may be configured to make an incision 4 millimeters in length, while the needle and/or sleeve may have a diameter of 1.8 millimeters.

Given that some fluids may leak out of the incision during aspiration, it is desirable to account for this leakage rate, to more accurately control aspiration and irrigation flow to prevent collapsing the eye or over-pressurizing the eye.

Where leakage occurs, the leakage rate of irrigation fluid from the incision 112 can be estimated by the present ophthalmic surgical system 100, which can predict leakage based in part on the size of the needle 128, the size of the sleeve 122, and size of the incision 112. Surgeons can enter these surgical parameters at the start of a procedure, to allow a predicted leakage to be estimated based on these parameters, and identified from a look up table based on the current infusion pressure. Alternatively, a predicted leakage can be estimated, or selected from a look-up table, based on the size of the needle, sleeve, incision, and an estimated intraocular eye pressure ($p_{eye}$) that is calculated assuming no leakage using equation (1).

To then account for leakage, the intraocular eye pressure $p_{eye}$ for the system in FIG. 1 can be represented by the equation:

$$p_{ib} - \Delta p_i = p_{eye} = \Delta p_a + p_v$$

where $p_{ib}$ is the pressure of the irrigation fluid in bottle 130, and $\Delta p_i$ is related to the leakage $Q_w$ and resistance $\Omega_i$ in the infusion line, as given by:

$$\Delta p_i = (Q + Q_w) \Omega_i$$

Likewise, $p_v$ is the pressure or vacuum at the collection reservoir 150, and $\Delta p_a$ is related to the resistance $\Omega_a$ in the aspiration line, as given by:

$$\Delta p_a = (Q \cdot \Omega_a)$$

By knowing the incision size, the needle cannula 128 inner and outer diameters, the sleeve 122 or sleeve diameter or cross-sectional area 126, and bottle height, the predicted wound leakage is estimated, and used to better control the intraocular pressure in the eye.

This predictor can be utilized in the control of intraocular pressure, as described by the methods shown in the flow charts in FIGS. 2 and 3, for example, which calculates aspiration resistance $\Omega_a$ from absolute pressure in the eye $P_{eye}$ based on aspiration flow, as shown in equation (2) below:

$$P_v = P_{eye} - (Q \cdot \Omega_a), \text{ or } \Omega_a = (P_{eye} - P_v)/Q \qquad \text{equation (2)}$$

The aspirated flow out of the eye, Q represents the flow into the eye minus the flow leakage. The vacuum pressure $p_v$ measured at the collection reservoir 150 (the pressure measured by transducer or sensor 160 associated with a vacuum pump device 140, for example) is equal to the pressure in the eye ($P_{eye}$) minus the pressure drop $\Delta p_a$ through the aspiration line, where $\Delta p_a$ equals the flow rate Q x the aspiration resistance $\Omega_a$. However, $\Omega_a$ is a dynamic variable based on occlusion, fluid density, and aspiration system compliance.

The present solution to predicting the intraocular pressure under leakage is to estimate the flow loss using a table based on wound size, needle, and estimated intraocular pressure. The initial estimated intraocular pressure default would assume no flow loss. The system would then measure the flow exiting the eye, e.g.—the combination of the aspiration flow rate Q and the predicted or estimated loss $Q_w$ (obtained from a look-up table), to arrive at the total flow rate and is equal to the irrigation flow entering the eye. This establishes a better estimate of $P_{eye}$ by using a more accurate Q in equation 1.

This initial estimate of $P_{eye}$ from eq. (1) can be used to calculate the aspiration resistance $\Omega_a$ using the sensed pressure reading $P_v$ and eq. (2). This calculated $\Omega_a$ can be used to monitor viscosity changes and occlusions. The initial estimate of $P_{eye}$ can also be used to refine the predicted flow leakage using the look-up table. By refining the leakage rate, the infusion flow rate into the eye can be again determined, and used in equation (1) to determine a refined intraocular pressure $P_{eye}$, which may be used to control irrigation flow for subsequently maintaining a constant desired pressure $P_{eye}$.

Figure 2:
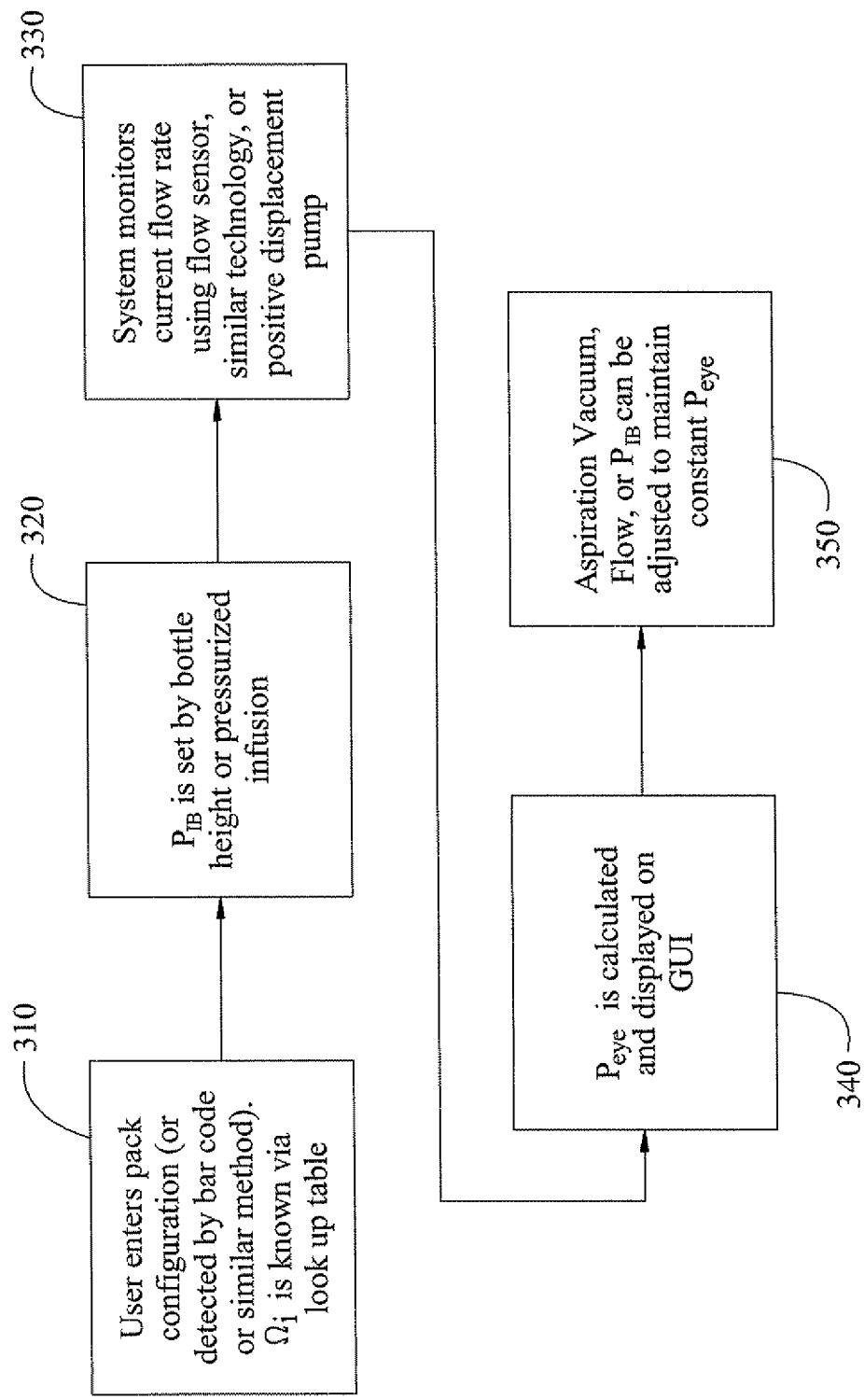
FIG. 2 is a functional block diagram of one embodiment of a method for a flow control system in accordance with one aspect of the present application.
Figure 3:
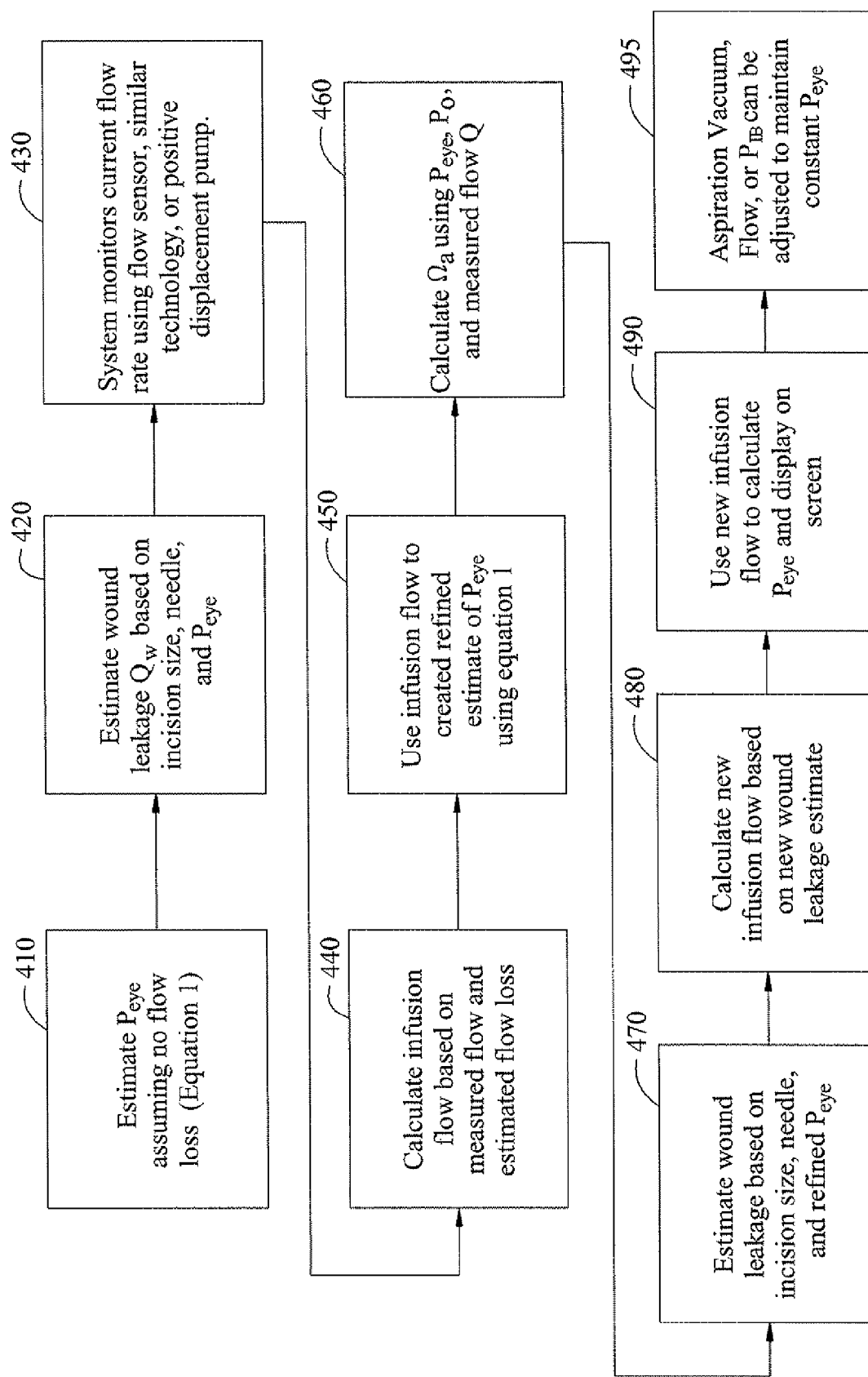
FIG. 3 is a functional block diagram of another embodiment of a method for a flow control system in accordance with one aspect of the present application.

To this end, the methods in FIGS. 2 and 3 take leakage into account to determine a more accurate flow rate Q, which is used in equation (1) to arrive at an initial estimate of the intraocular pressure $P_{eye}$ that accounts for leakage. Referring to FIG. 3, after the intraocular pressure $P_{eye}$ is estimated at step 410 using equation (1), the predicted leakage $Q_w$ from the wound is identified in a look up table based on the incision, needle and sleeve size, and the initial estimate or measurement of the intraocular eye pressure $P_{eye}$. The system then monitors the aspiration fluid flow rate at step 430, using a positive displacement pump, a flow sensor, electromagnetic flow technology, or other similar flow sensing technology. At step 440, the method calculates the infusion flow rate entering the eye 110 based on the measured aspiration flow rate and the predicted flow loss (leakage) or loss rate.

The method then takes the calculated infusion flow rate Qi from step 440, and uses it, at step 450, in equation (1) for estimating a more refined intraocular pressure $P_{eye}$. This calculation of a refined $P_{eye}$ using a more accurate determination of Q that includes the leakage provides a better estimate of $P_{eye}$. From the refined $P_{eye}$, the controller 200 can calculate, at step 460, the aspiration flow resistance $\Omega_a$ from equation (2), using the pressure $P_{eye}$, the pressure $P_o$, and measured flow Q. At step 470, the method estimates or looks up leakage Qw again from a look-up table, and calculates, at step 480, a new infusion flow which is used to calculate yet another more accurate intraocular pressure $P_{eye}$, at step 490. Once the Intraocular pressure $P_{eye}$ is determined, the aspiration flow vacuum $P_o$, flow Q, or infusion pressure $P_{ib}$ can be adjusted to maintain a constant intraocular pressure $P_{eye}$.

Figure 4:
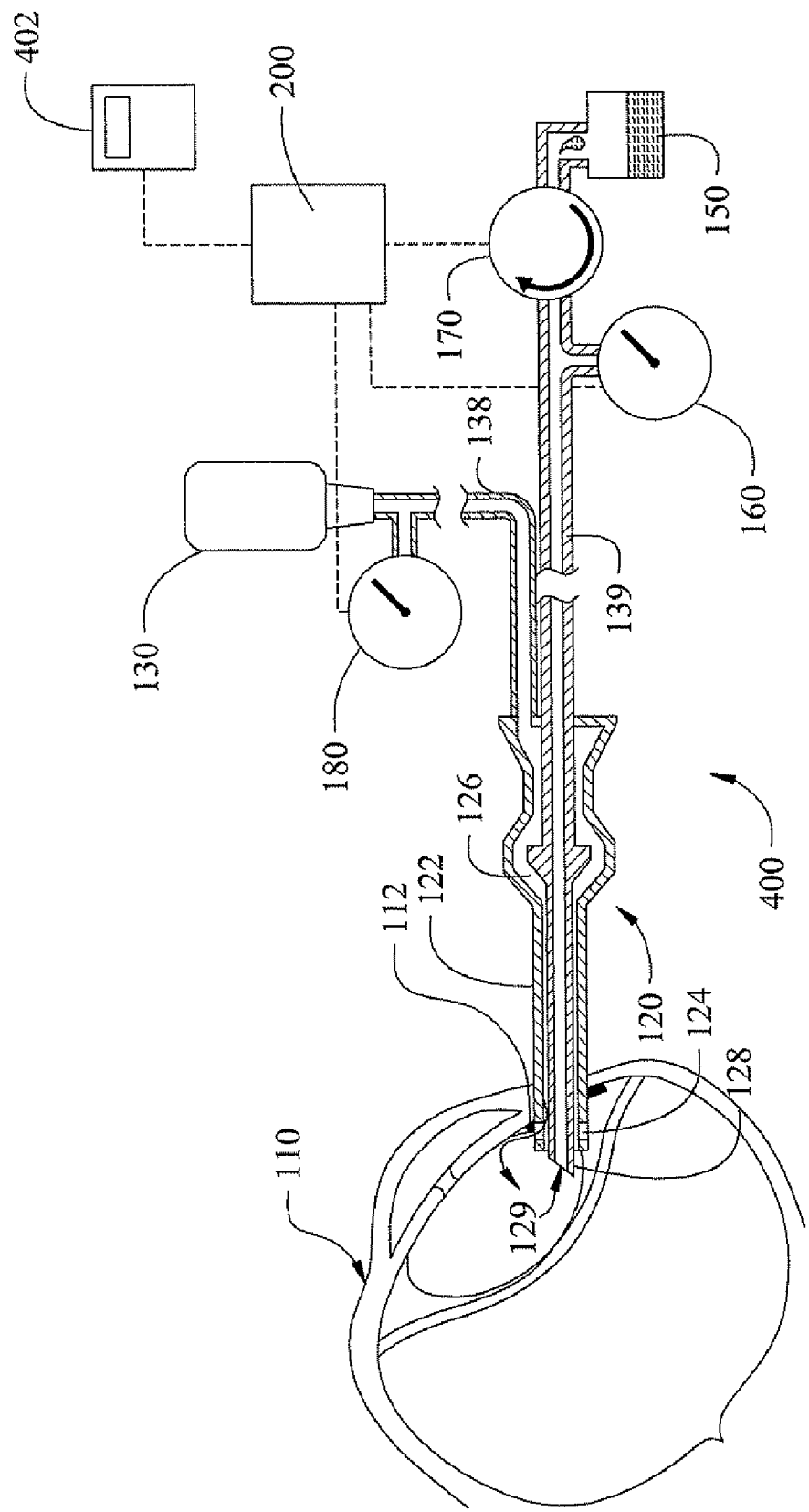
FIG. 4 shows a cross-sectional perspective view of one embodiment of a needle and aspiration flow control system in accordance with the present invention.

Referring to FIG. 4, a second embodiment of an ophthalmic surgical system is shown. The system 400 is similar in many respects to the embodiment in FIG. 1. The system 400 generally comprises an ophthalmic device 120 that includes a needle 128 having a needle passage 129 through which fluid is aspirated from a surgical site. The ophthalmic device 120 includes a sleeve 122 coaxially extending over the needle 128 so as to define a flow passage 126 between the sleeve 122 and the needle 128, through which passage 126 irrigation fluid is communicated to a surgical site. The ophthalmic device 120 is configured to be inserted into a medium (such as an eye 110) through an incision 112 of a predetermined size.

The system 400 provides for irrigation flow to the eye using an irrigation line 138, through which irrigation fluid is communicated between a fluid container 130 and the sleeve 122.

The fluid container 130 is configured to provide an adjustable infusion pressure for urging flow of irrigation fluid through the irrigation line 138 and sleeve 122 to the surgical site, either by adjusting the elevation of the container 130 or by adjusting the pressure in the container. The system 400 may further include a measuring device 180 for measuring a value indicative of the infusion pressure at the fluid container 130. It should be noted that the infusion pressure at the container 130 may be determined simply by measuring a value indicative of the infusion pressure, such as the container height, or by a measuring device 180 that senses pressure.

The system 400 provides for aspiration of fluids from the eye using an aspiration line 139, through which fluid is communicated between the needle passage 129 of the needle 128 and an aspiration pump 170. A pump 170 is provided that is configured to establish a vacuum or flow rate, which is applied to urge the flow of fluid aspirated from a surgical site through the needle 128 and aspiration line 139. A pressure sensing device 160 or transducer is provided for generating a signal indicative of the level of vacuum being applied by the pump 170. Similarly, a flow sensing device may be provided for generating a signal indicative of the flow rate of fluid being aspirated from the surgical site. It should be noted that the flow rate may be sensed or monitored by a positive displacement pump 170, or may alternatively be monitored by a flow sensor, electromagnetic flow technology, or other similar flow sensing technology.

The system 400 may further include a user interface 402 for entering the information of the needle size, sleeve size, and predetermined size of the incision. The system 400 further includes a controller 200 in communication with the user interface 402, pressure sensing device 160, the vacuum pump and/or the flow sensing device 170, and second pressure sensing device 180. The control 200 is configured to calculate an intraocular eye pressure based on the sensed infusion pressure less the pressure drop caused by a predetermined resistance to the irrigation fluid flow, which flow is determined as a combination of a sensed fluid flow rate and a predicted leakage rate of fluid exiting the incision. The predicted leakage rate of fluid exiting the incision is selected from a look-up table of the controller, based on at least the needle size, sleeve size, incision size, and infusion pressure. Alternatively, a predicted leakage can be estimated, or selected from a look up table, based on the size of the needle, sleeve, incision, and an estimated intraocular eye pressure ($p_{eye}$) that is calculated assuming no leakage using equation (1). The controller 200 may then adjust the infusion pressure, or vacuum pump 170, or both, based on the calculated intraocular eye pressure, to thereby maintain a desired intraocular eye pressure.

The controller 200 may be further configured to calculate a more refined intraocular eye pressure. As outlined in FIG. 3, the calculation of a refined intraocular eye pressure is based on infusion pressure less the pressure drop due to the predetermined resistance to irrigation flow, as determined by a combination of the sensed fluid flow rate and a predicted leakage rate that is selected from a look-up table based on needle size, sleeve size, incision size, and the initially estimated intraocular eye pressure. The controller 200 may be further configured to determine an aspiration flow resistance based on the determined intraocular pressure, the vacuum pressure applied by the vacuum source, and the sensed fluid flow rate, whereby the aspiration flow resistance is used by the controller to monitor occlusions.

In another aspect of the present application, embodiments of a method for controlling an ophthalmic surgical system to control fluid flow are provided, for maintaining intraocular pressure in an eye. In one embodiment, the method for controlling the operation of a controller for regulating irrigation flow through an ophthalmic device in an ophthalmic surgical system comprises receiving the input of a needle size, a sleeve size, and an incision size, and identifying a predetermined resistance to irrigation fluid flow associated with the ophthalmic device. The method performs the steps of obtaining a variable that is indicative of the infusion pressure of irrigation fluid at an elevated container, and selecting a predicted leakage rate of fluid exiting the incision from a look-up table, based on the needle size, sleeve size, incision size, and infusion pressure. The method then calls for sensing a fluid flow rate of irrigation fluid as detected by a flow sensor, and determining an intraocular eye pressure based on the sensed infusion pressure less the pressure drop caused by a predetermined resistance to the irrigation fluid flow. The irrigation fluid flow is determined as a combination of a sensed fluid flow rate and a predicted leakage rate of fluid exiting the incision, where the predicted leakage rate of fluid exiting the incision is selected from a look-up table based on the needle size, sleeve size, incision size, and infusion pressure.

In another embodiment of a method for controlling an ophthalmic surgical system to control fluid flow are provided, for maintaining intraocular pressure in an eye. In one embodiment, the method for controlling the operation of a controller for regulating irrigation flow through an ophthalmic device in an ophthalmic surgical system comprises receiving the input of a needle size, a sleeve size, and an incision size, and identifying a predetermined resistance to irrigation fluid flow associated with the ophthalmic device. The method performs the steps of obtaining a variable that is indicative of the infusion pressure of irrigation fluid at an elevated container, and sensing the fluid flow rate of irrigation fluid detected by a flow sensor, for use in estimating an intraocular eye pressure value, based on the sensed infusion pressure less the pressure drop caused by a predetermined resistance to fluid flow. The estimation of an intraocular eye pressure value is based on a fluid flow determined only from the sensed fluid flow rate detected by the flow sensor, and does not include any predicted leakage flow. The method then calls for selecting a predicted leakage rate from a look-up table based on needle size, sleeve size, incision size and the estimated intraocular eye pressure value, for use in calculating a refined intraocular eye pressure. The refined intraocular eye pressure is calculated based on the sensed infusion pressure less the pressure drop caused by a predetermined resistance to the irrigation fluid flow, which flow is determined as a combination of a sensed fluid flow rate and the predicted leakage rate of fluid exiting the incision that was selected from the look-up table. In either embodiment, the method may then use the determined intraocular eye pressure for subsequently controlling the flow of irrigation fluid in the system, based on the refined intraocular eye pressure, to thereby maintain a desired intraocular eye pressure.

From the above, it may be appreciated that the present invention provides improved apparatus and methods of performing vitrectomy surgery. The present invention is illustrated herein by example, and various modifications may be made by a person of ordinary skill in the art.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A system for regulating pressure in an ophthalmic surgical system comprising:
- a sleeve coaxially received over a needle so as to define a flow passage between the sleeve and the needle through which irrigation fluid is communicated to a surgical site, and a needle passage through which fluid is aspirated from the surgical site, the sleeve and needle for insertion into a medium through an incision of a predetermined size;
- a container configured to provide an adjustable infusion pressure for urging a flow of irrigation fluid within the container to the sleeve, for infusion to the surgical site;
- a vacuum source configured to establish a vacuum for urging an aspiration of fluid from the surgical site through the needle passage;
- a sensor for providing a signal indicative of the vacuum being applied;
- a flow sensing or estimating device for providing a signal indicative of a flow rate of fluid being aspirated from the surgical site; and
- a controller configured to receive an input of a needle size, a sleeve size, and the incision size, and to estimate an intraocular eye pressure based on the infusion pressure less a pressure drop due to a predetermined resistance to the fluid flow, which fluid flow does not include any predicted leakage flow and wherein the controller is configured to obtain a more refined estimate of the intraocular eye pressure based on the infusion pressure and a combination of the sensed fluid flow rate and a predicted leakage rate of fluid exiting the incision selected from a look-up table based on the needle size, the sleeve size, and the incision size, wherein the controller uses the refined estimate to control fluid flow to maintain a desired intraocular pressure.

2. The system of claim 1, wherein the controller is further configured to determine an aspiration flow resistance based on the refined intraocular pressure, the vacuum applied by the vacuum source, and the sensed or estimated fluid flow rate, whereby the aspiration flow resistance is used by the controller to monitor occlusions.

3. The system of claim 1 further comprising a vacuum sensor for sensing a level of vacuum applied by the vacuum source for establishing aspiration of fluid flow from the surgical site.

4. The system of claim 1, wherein the vacuum source is a vacuum pump, which the controller is configured to control to adjust the level of vacuum applied by the vacuum pump for controlling the flow rate of fluid being aspirated from the surgical site.

5. The system of claim 1, wherein a height of the container may be altered to adjust the infusion pressure of the irrigation fluid in the container.

* * * * *